Aug. 19, 1947. H. M. EDDIE Plant Pat. 753
ROSE PLANT
Filed Jan. 2, 1946
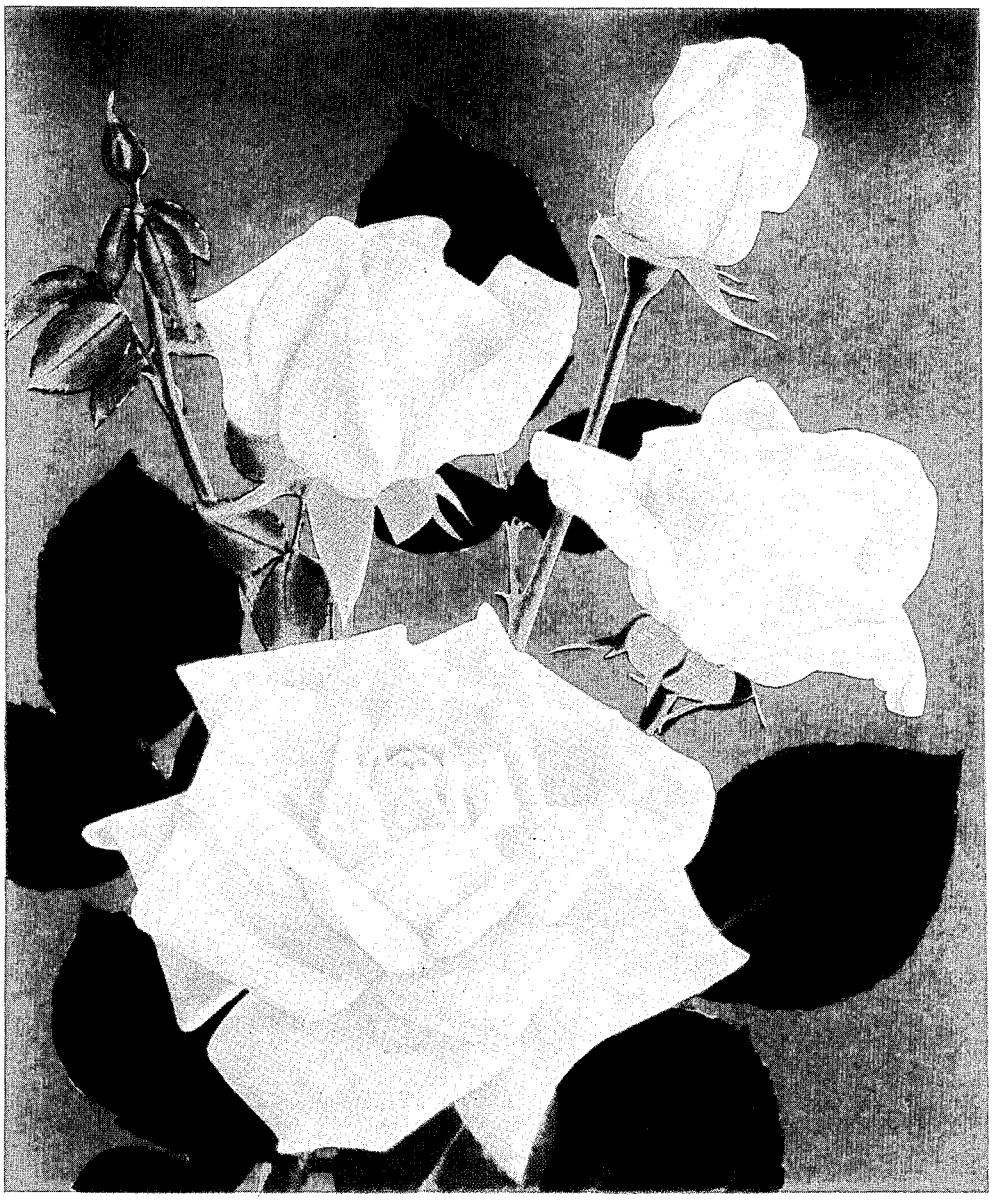
INVENTOR
Henry Matheson Eddie
By Orville M. Kile
Plant Pat. Agt.

Patented Aug. 19, 1947

Plant Pat. 753

UNITED STATES PATENT OFFICE

753

ROSE PLANT

Henry Matheson Eddie, near Sardis, British Columbia, Canada, assignor to H. M. Eddie and Sons Limited, New Westminster County, British Columbia, Canada, a corporation of British Columbia Application January 2, 1946, Serial No. 638,650

1 Claim. (Cl. 47—61)

My present invention is an improvement in hybrid tea rose plants and consists of a new and distinct variety obtained by crossing Mrs. Chas. Lamplough and Mrs. G. A. Van Rossem. This cross was performed by me at my greenhouses in British Columbia several years ago. Asexual reproduction of this variety by budding has shown its distinctive characteristics to be transmitted in full and firmly fixed.

The blooms of this variety are essentially white although they are enhanced by faint tints of pink and by lemon yellow suffusing from the base upward. Other outstanding qualities of the variety are its sturdy growth, the heavy texture of petals and foliage, and the slow and perfect opening of the bud into full flower even in wet weather.

The accompanying illustrations show several specimens of the flowers of this new variety in various stages of opening, together with portions of the foliage and stems.

Following is a detailed description of the plant and flower:

*The Plant*

Growth:

*Form.*—Stocky, upright bush which branches freely.

*Vigor.*—Very sturdy and strong.

*Disease resistance.*—Very resistant to mildew and other common diseases of roses.

*Blooming habit.*—Bud opens slowly and perfectly, taking five to seven days to fully open after first petals begin to unfurl. Blooming is continuous.

Foliage:

*Leaflets.*—Five.

*Quantity.*—Abundant.

*Size.*—Leaves 5 to 6 inches long. Terminal leaflets 2½ to 3 inches long.

*Shape.*—Broadly oval with sharp apex.

*Edge.*—Slightly serrated.

*Colour.*—Very dark, rich green. New foliage russet.

*Substance.*—Heavy.

*Rachis or midrib.*—Grooved above. Almost thornless, with only an occasional small spine on under side.

*Stipules.*—Narrow. Nearly adherent to first set of leaflets.

Stems:

*Strength.*—Very sturdy.

*Internodes.*—Short.

*Colour.*—Medium green with bluish green tinge when young.

*Thorns.*—Moderate quantity. Large; triangular; slightly downward hooked. Pinkish in colour.

*The flower*

Bud:

*Size.*—When beginning to open, bud is approximately 1½ inches long from top of ovary. It is 1½ inches wide at its base.

*Shape.*—Wide at base, tapering to point.

*Colour.*—Old ivory, with shadings of lemon at base.

*Calyx.*—Composed of five broad sepals which turn backward early. Usually simple but sometimes slightly foliaceous. Slightly hirsute. Light green tinged with pink.

*Peduncle.*—Very stiff, strong, and erect. Short and thickly studded with fine spines. Holds large flowers perfectly erect and close to foliage.

*Opening.*—Slow and perfect, unfolding over a period of several days. Buds do not "ball" in wet weather; develop perfectly in hottest weather.

Bloom:

*Size.*—Large, averaging 5 or 6 inches in diameter, often attaining 7 inches.

*Form.*—Broad at base, rising to a high centre which is held throughout most of the life of the flower. Outer petals reflex at edges, giving them a pointed effect which makes a beautiful frame for the high centre. Later all petals recurve to form sharp points.

*Colour.*—General colour effect is of a white rose with lemon yellow and faint pink shadings. Centre of flower is pale yellow, base of petals deeper yellow and extreme ends white, with occasional faint pink.

*Quantity.*—Flowers are produced in fair abundance and continue late in the fall.

*Fragrance.*—Slightly tea.

*Petalage.*—Very double, with 40 to 45 petals.

*Longevity.*—Longevity on the bush is one of this variety's outstanding features. A period of 6 or 7 days elapses from the time the first petals unroll until the flower reaches its peak of perfection. Flowers also last well when cut.

Petals:

*Shape.*—Broad, almost round when flattened.

*Size.*—Outer petals 2½ inches by 2¼ inches in diameter.

*Texture.*—Very heavy.

*Colour.*—White to ivory, with large base of lemon yellow which suffuses upward. Edges of petals often faintly tinted with pink.

*Appearance.*—Satiny on both surfaces.

Reproductive organs:

*Pistils.*—Bunched; elevated on styles.

*Stamens.*—Golden yellow; surround pistils.

Fruit:

Very large, oblate spheroid, rough and ribbed.

*Comparison*

The variety most like my new variety is one of its parents, Mrs. Chas. Lamplough, but it differs from that variety principally in the following respects.

1. My new variety makes a more sturdy, stocky growth.
2. It has larger and darker coloured foliage.
3. Its neck or peduncle is much stronger and more upright.
4. Texture of its petals is much heavier.
5. Its petals are more fully recurved.
6. Its flower opens more perfectly and more slowly.
7. Its flowers do not "ball" in wet weather as do those of the variety Mrs. Chas. Lamplough.

8. Its flower is much longer lasting.

Having thus disclosed my invention, I claim:

The new and distinct variety of rose plant substantially as herein disclosed, characterized by its stocky and sturdy growth, its great resistance to disease, its abundant large dark green foliage, its strong peduncle, the slow and prolonged opening of its buds resulting in very great longevity, the perfect opening of the buds without balling in wet and hot weather, and its large well-formed flowers essentially white in colour with recurved petals and high centers, said petals having heavy texture and satiny appearance.

HENRY MATHESON EDDIE.

REFERENCES CITED

The following references are of record in the file of this patent:

UNITED STATES PATENTS

| Number | Name | Date |
|---|---|---|
| Pl. Pt. 49 | Grillo | Dec. 20, 1932 |
| Pl. Pt. 108 | Lens | Oct. 16, 1934 |
| Pl. Pt. 335 | Johnston | July 18, 1939 |